US00PP09779P

United States Patent [19]

Apps

[11] Patent Number: Plant 9,779

[45] Date of Patent: Jan. 7, 1997

[54] DAYLILY NAMED 'ROSY RETURNS'

[75] Inventor: Darrel A. Apps, Bridgeton, N.J.

[73] Assignee: Centerton Nursery, Inc., Bridgeton, N.J.

[21] Appl. No.: 554,005

[22] Filed: Nov. 6, 1995

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Burns, Doane, Swecker & Mathis, L.L.P.

[57] ABSTRACT

A new and distinct Hemerocallis cultivar of the dormant type named 'Rosy Returns' is provided. The new cultivar is very floriferous and forms attractive rose-pink blossoms over an extended period of time that commonly begins during late May to early June and commonly ends during late September to early October in Zone No. 6. The new plant readily forms fans and readily forms a number of scapes per fan. The new cultivar is particularly well suited for growing as distinctive colorful ornamentation in the landscape.

1 Drawing Sheet

SUMMARY OF THE INVENTION

The present invention comprises a new and distinct cultivar of Hemerocallis of the dormant type, and hereinafter is referred to by the cultivar name 'Rosy Returns'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during July, 1993, at Chadds Ford, Pa. U.S.A. The female parent (i.e., the seed parent) of the new cultivar was created by the following crosses:

('Pardon Me'×'Happy Returns')×('Happy Returns'×'Sugar Cookie').

The female parent formed a 6 to 6.5 cm. dirty brick red flower of poor substance. The male parent (i.e., the pollen parent) of the new cultivar was created by the following crosses:

[('Brocaded Gown'×'Happy Returns') onto ('Pardon Me'×'Happy Returns')]×('Happy Returns'×'Sugar Cookie').

The male parent formed 6 to 6.5 cm. inch plain yellow fluted flowers. Each of the above-named cultivars in the ancestry of the new 'Rosy Returns' cultivar is non-patented in the United States and is registered with the American Hemerocallis Society.

The seeds resulting from the above pollination were sown and small plantlets were obtained which were physically and biologically different from each other. A number of such plants were transplanted to Bridgeton, N.J., U.S.A. during early 1994. Selective study during July 1995 resulted in the identification of a single plant of the new cultivar.

It was found that the new Hemerocallis cultivar of the present invention is of the dormant type and:

(a) forms attractive rose-pink flowers having a substantial substance and a flat form,
(b) possesses a long blooming season with substantially continuous blooming,
(c) exhibits a propensity to readily display a plurality of fans, and
(d) readily forms a plurality of scapes per fan over the flowering season.

The 'Rosy Returns' cultivar resembles some well-known cultivars, such as the 'Stella De Oro' cultivar (non-patented in the United States) and the 'Happy Returns' cultivar (non-patented in the United States) in the sense that it commonly possesses an extremely long and substantially continuous blooming season of up to approximately 125 days in USDA hardiness Zone No. 6. Such blooming commonly begins during late May to early June and commonly ends during late September to early October. This compares to a bloom period of less than about 30 days for over 99 percent of the hybrid Daylilies that are presently available.

As indicated, 'Rosy Returns' exhibits attractive rose-pink flowers that readily can be distinguished from the orange-yellow flowers of the 'Stella De Oro' cultivar and the medium yellow flowers of the 'Happy Returns' cultivar. To the best of the knowledge of the originator 'Rosy Returns' is the first long and substantially continuously blooming Daylily having flowers that exhibit a rose or pink hue.

The new cultivar can form up to 14 or more fans per year. This compares to approximately 6 to 8 fans per year for the 'Stella De Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Sep. 8, 1995 at Bridgeton, N.J., U.S.A. At the time of such asexual reproduction the original plant of the new cultivar consisted of a clump of fourteen fans that were phenotypically identical to each other. More specifically, the clump of the new cultivar was removed from the field and the fans were divided. It has been demonstrated that the characteristics of the new cultivar are firmly fixed and are well retained following this asexual reproduction.

'Rosy Returns' has not been observed under all possible environmental conditions to date. Accordingly, it is possible that the phenotype may vary somewhat with variations in the environment, such as temperature, light, day length, contact with pesticides, etc.

It is contemplated that the new cultivar will be marketed while bearing the HAPPY EVER APPSTER trademark.

BRIEF DESCRIPTION OF THE PHOTOGRAPHS

The accompanying photographs were prepared during the late August to early September 1995 time period, and show as nearly true as it is reasonably possible to make the same in color illustrations of this character, the original plant and flower of the new cultivar of the present invention. The plant was being grown outdoors in the field at Bridgeton, N.J., U.S.A.

DETAILED DESCRIPTION

The chart used in the identification of colors described herein is the R.H.S. Colour Chart of The Royal Horticultural Society, London, England. In some instances, more common color terms are provided and are to be accorded their usual dictionary significance. The original plant of the new cultivar is described when observed during early September 1995 while growing at Bridgeton, N.J., U.S.A. under field growing conditions.

Classification:

*Botanical.*—Hemerocallis hybrid, cv. 'Rosy Returns'.

*Commercial.*—Daylily.

Figure 1:
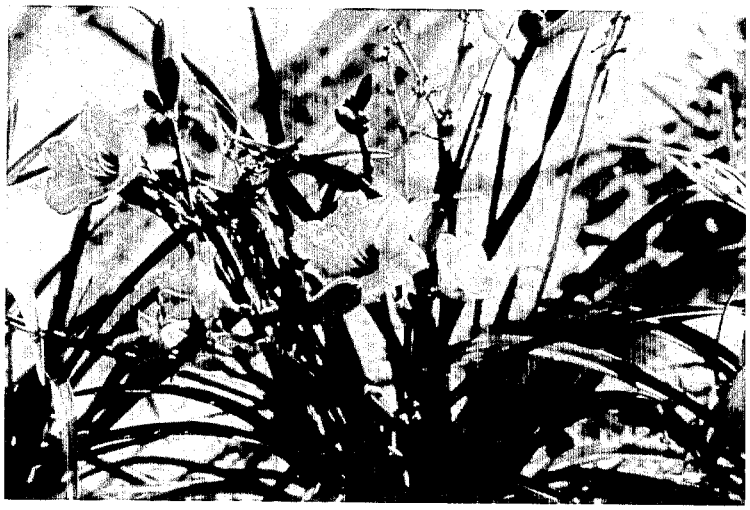
FIG. 1 illustrates the plant clump with foliage, buds, and flowers in various stages of maturity.
Figure 2:
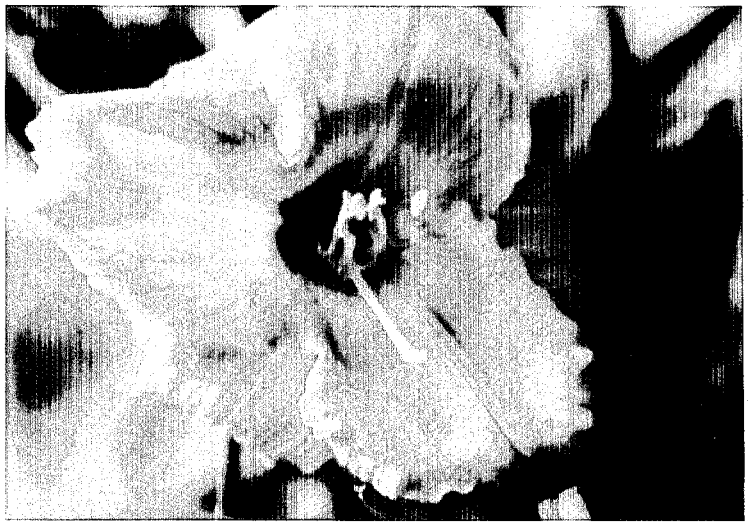
FIG. 2 illustrates a close up view of a mature flower of the present invention wherein the stamens and pistil are visible.

Plant:

*Foliage.*—Form: single stem, substantially erect shapes from a fan-shaped plant having narrow arching, long, keeled, grass-like glabrous leaves that are two-ranked at the base of the scape. Quantity: abundant, with a mature plant commonly having approximately 12 to 14 leaves per fan. Leaf size: commonly approximately 1.3 cm. in width on average and approximately 31 cm. in length on average. Leaf shape: linear and long-keeled (as illustrated in FIG. 1) with entire margins. Texture: glabrous. Color: medium green, Yellow-Green Group 146A. Type: dormant with the plant losing all of its foliage during the winter.

*Scape.*—Color: Lettuce Green, Yellow-Green Group 144A. Height: commonly approximately 40 cm. on average.

*Disease resistance.*—Typical of Hemerocallis with no problems having been observed to date.

Inflorescence:

*Bud.*—Form: modified oblanceolate (as illustrated in FIG. 1). Size: on the day prior to opening commonly approximately 6 cm. in length on average and approximately 1.2 cm. in width on average. Opening rate: commonly approximately three hours on average. Sepal color: when sepals first divide, Lettuce Green, Yellow-Green Group 144A. Peduncle character: rigid and sturdy. Peduncle color: medium green, Green Group 138A.

*Flower.*—Size: commonly has a diameter of approximately 11 cm. on average and a depth of approximately 5 cm. on average. Borne: singly on the branchlets of a sturdy erect rachis which is ramulose. Each scape commonly has at least three peduncles, each of which divides into approximately ten pedicels. Blooms per scape: Commonly ranges from 1 to 3 each day. Petalage: each flower consists of six perianth segments wherein there are three sepals (outer segments) and three petals (inner segments) all in an imbricated arrangement. Sepal shape: Oblanceolate with slightly undulated entire margins and an acuminate apex. Sepal texture: Ribbed. Sepal size: commonly approximately 6.8 cm. in length on average and approximately 3.3 cm. in width on average. Sepal color: rose-pink, Red-Purple Group 67D with a dusting of Red-Purple Group 67A on the sepal at a diametric point coordinating to the petal's eye zone and mostly hidden by the overlapping petals. Petal shape: broadly obovate with entire undulated margins and a broadly cuspidate apex. Petal texture: slightly puckered and ribbed. Petal size: commonly approximately 7 cm. in length on average and approximately 5.5 cm. in width on average. Petal color: rose-pink, Red-Purple Group 67D with an eye zone of Red-Purple Group 67A, a yellow throat approaching Yellow Group 6C, and an innermost throat of Yellow-Green Group 154A. Blooming habit: the flowers commonly bloom substantially continuously and the scape commonly is substantially continuously in bloom for up to approximately 125 days per year in Zone No. 6. Based on the parentage and observations of the new cultivar to date it is anticipated that the plant will perform satisfactorily in Zone Nos. 4 through 9. Effects of weather: the flowers well withstand rain damage in view of the strength of the petals. Lasting quality: commonly at least 16 hours. As with other Hemerocallis cultivars, the flower color eventually fades somewhat during the day with the natural effects of environmental conditions and ongoing maturity. Fragrance: slight.

*Reproductive organs.*—Stamen number: six per flower. Stamen disposition: individually inserted at the summit of the perianth tube. Anther disposition: introrse. Anther size: approximately 0.8 cm. in length. Anther color: Grey-Brown Group 199B. Filament configuration: slender. Filament length: commonly approximately 4.8 cm. on average. Filament color: rose-pink, Red-Purple Group 67D. Pollen color: Yellow Group 6C. Pistil number: one per flower. Style length: approximately 6 cm. in length on average. Style color: rose-pink, Red-Purple Group 67D. Stigma color: Yellow Group 6C. Ovaries: three-celled, oblong, and becoming a loculiedally three-valved capsule.

*Fruit.*—Configuration: the seed pod is in the form of an ovoid capsule. Color: at maturity commonly ranges between Yellow-Green Group 144A and Greyed-Green Group 197B. Fertility: the seeds are fertile.

I claim:

1. A new and distinct cultivar of Hemerocallis of the dormant type, substantially as herein shown and described, which (a) forms attractive rose-pink flowers having a substantial substance and a flat form, (b) possesses a long blooming season with substantially continuous blooming, (c) exhibits a propensity to readily display a plurality of fans, and (d) readily forms a plurality of scapes per fan over the flowering season.

* * * * *